(12) United States Patent
Vennard et al.

(10) Patent No.: US 9,968,348 B2
(45) Date of Patent: May 15, 2018

(54) SURGICAL ACCESS TUBE (71) Applicant: DePuy Synthes Products, Inc., Raynham, MA (US)

(72) Inventors: Daniel Vennard, West Chester, PA (US); William Miller, West Chester, PA (US); Hewatt McGraw Sims, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 217 days.

(21) Appl. No.: 13/775,571

(22) Filed: Feb. 25, 2013

(65) Prior Publication Data
US 2014/0243604 A1 Aug. 28, 2014

(51) Int. Cl.
*A61B 1/32* (2006.01)
*A61B 17/02* (2006.01)

(52) U.S. Cl.
CPC ...... *A61B 17/0218* (2013.01); *A61B 17/0293* (2013.01)

(58) Field of Classification Search
CPC ............ A61B 17/3423; A61B 17/3498; A61B 17/3445; A61B 17/34922; A61B 1/32; A61B 17/02; A61B 17/0206; A61B 17/0218; A61B 17/0293; A61B 17/3425; A61B 17/2439
USPC ............................... 600/208, 201; 606/86 A
See application file for complete search history.

(56) References Cited

U.S. PATENT DOCUMENTS

| | | | | |
|---|---|---|---|---|
| 3,528,424 A | * | 9/1970 | Ayres | ............................. 606/19 |
| 4,834,067 A | * | 5/1989 | Block | ...................... A61B 1/31 |
| | | | | 600/184 |
| 5,391,156 A | | 2/1995 | Hildwein et al. | |
| 5,425,357 A | * | 6/1995 | Moll | .................. A61B 17/0218 |
| | | | | 600/207 |
| 5,490,843 A | | 2/1996 | Hildwein et al. | |
| 5,776,110 A | | 7/1998 | Guy et al. | |
| 5,803,904 A | * | 9/1998 | Mehdizadeh | ................. 600/235 |
| 5,830,191 A | | 11/1998 | Hildwein et al. | |
| 5,900,971 A | * | 5/1999 | Ning | ............................. 359/435 |
| 6,126,594 A | * | 10/2000 | Bayer | ...................... A61B 1/31 |
| | | | | 600/184 |
| 6,916,330 B2 | | 7/2005 | Simonson | |
| 6,958,037 B2 | | 10/2005 | Ewers et al. | |
| 7,008,431 B2 | | 3/2006 | Simonson | |
| 7,029,438 B2 | * | 4/2006 | Morin | ................ A61B 1/00073 |
| | | | | 600/184 |

(Continued)

*Primary Examiner* — Jacqueline Johanas
*Assistant Examiner* — Tessa Matthews
(74) *Attorney, Agent, or Firm* — Meunier Carlin & Curfman LLC (57) ABSTRACT

Implementations of the present disclosure provide an access tube including a wall structure and an optional handle extending from the wall structure. Selectively weakened areas facilitate selective resection of the wall structure to reveal windows that accommodate lateral intrusions by surrounding anatomical structures and/or provide increased access to an intervertebral disc. For example, a first distal weakened portion is configured to form a first window to afford lateral intrusion of a spinous process. A second distal weakened portion is configured to form a second window to afford lateral intrusion of facet. A proximal weakened portion is configured to afford additional angular access on a proximal end of the tube.

42 Claims, 9 Drawing Sheets

(56) References Cited

U.S. PATENT DOCUMENTS

| | | |
|---|---|---|
| 7,238,154 B2 | 7/2007 | Ewers et al. |
| 7,377,898 B2 | 5/2008 | Ewers et al. |
| 7,824,410 B2 | 11/2010 | Simonson et al. |
| 8,131,380 B2 * | 3/2012 | Cao ........................ A61N 1/205 607/138 |
| 8,430,814 B2 * | 4/2013 | Bozdag ................... A61B 1/31 600/245 |
| 8,585,719 B2 * | 11/2013 | Chen et al. ................... 606/148 |
| 2003/0130559 A1 * | 7/2003 | Morin ................ A61B 1/00073 600/104 |
| 2004/0049099 A1 | 3/2004 | Ewers et al. |
| 2005/0288558 A1 | 12/2005 | Ewers et al. |
| 2006/0009797 A1 * | 1/2006 | Armstrong ......... A61B 1/00071 606/197 |
| 2006/0106416 A1 * | 5/2006 | Raymond et al. ............ 606/198 |
| 2007/0225568 A1 | 9/2007 | Colleran |
| 2007/0225569 A1 | 9/2007 | Ewers et al. |
| 2007/0270866 A1 | 11/2007 | von Jako |
| 2008/0200767 A1 | 8/2008 | Ewers et al. |
| 2008/0249372 A1 * | 10/2008 | Reglos et al. ................ 600/205 |
| 2009/0312745 A1 * | 12/2009 | Goldfarb et al. ............ 604/514 |
| 2011/0021879 A1 | 1/2011 | Hart et al. |
| 2011/0040333 A1 | 2/2011 | Simonson et al. |
| 2011/0087075 A1 * | 4/2011 | Wenchell et al. ............ 600/235 |
| 2011/0118552 A1 | 5/2011 | Fischvogt |

\* cited by examiner

SURGICAL ACCESS TUBE

BACKGROUND

Herniation of an intervertebral disc often presses on adjacent nerves causing pain and numbness. Surgery to resect the herniation and provide clearance for the nerves is one solution. However, access to the disc is limited by important surrounding anatomy including the spinous process, lamina and facets.

Discectomy tubes are cylindrical tubes employed to facilitate surgical access for surgery on intervertebral discs. These tubes are inserted through a skin incision and push away muscle and other intervening tissues to provide a pathway to the disc. Placement of such tubes is often lateral of the spinous process because the distal end of the discectomy tube is blocked by the spinous process. The end result is that only a lateral portion of the tube is providing access to the disc and most instrumentation has to extend through the tube at a sharp angle, reducing the effectiveness of the tube.

Some surgeons address this problem by selectively resecting some portion of the distal end of the tube to afford clearance for the spinous process. This allows the tube to be axially oriented more directly toward the herniation. However, selective resection of the tube can be tedious and haphazard resulting in less-optimal surgical working conditions.

Improvements in discectomy tubes are therefore desired.

SUMMARY

Implementations of the present disclosure overcome the problems of the prior art by providing a tube for facilitating access to an intervertebral disc (or other anatomical structure) through intervening anatomical structures, such as skin and soft tissue, and adjacent anatomical structures. Included in the tube is a wall structure comprised of material sufficiently stiff to define and hold open a tube opening to the disc through intervening skin and soft tissue. The wall structure includes a proximal edge and a distal edge and a length extending therebetween. At least one selectively weakened distal portion extends from the distal edge of the wall structure. The selectively weakened distal portion is configured for separation from a remainder of the wall structure to form a window shaped to accommodate lateral intrusion into the tube opening of at least one of the anatomical structures.

Also included may be at least one selectively weakened portion on the proximal edge of the wall structure that's configured to increase a viewing angle through the tube. For example, the selectively weakened proximal and distal portions may be configured to allow 30 degrees of viewing angle from the proximal edge. Also, the selectively weakened proximal portion may be positioned opposite of the selectively weakened distal portion and have a maximum height of 20 mm or even 30 mm.

The selectively weakened distal portion may be positioned to create a window for a facet and a second selectively weakened distal portion positioned to create a window for a spinous process. These windows are positioned on opposite sides of the wall structure and may be symmetrical or asymmetrical. The spinous process window may have a height of half or less that of the spinous process. The spinous process window, for example, may be 20 min or less. For the asymmetrical configuration, the facet window has a height of 10 mm or less.

The spinous process window may be configured to accommodate a spinous process/lamina tapered region. Also, the spinous process window may have a proximal arc shape, such as an arc shape with a radius of up to 10 mm. The radius of the proximal arc may be up to 5 mm, or even 10 mm. For example, the radius of the proximal arc may be 6 mm. The facet window may also have a proximal arc shape wherein the radius up to 5 mm or 10 mm.

The selectively weakened distal portion(s) may encompass a total of at least 110 degrees of the distal edge. Also, the selectively weakened portion may extend through a full thickness of the walls structure.

The length of the tube is preferably 90 mm, or 70 mm or less and the walls structure is cylindrical and has a diameter of 19 mm or less.

The tube may be used in a method of accessing an intervertebral disc. For example, the method may include selectively separating a first weakened portion from a remainder of a wall structure of the tube to form a first window extending from a distal edge of the wall portion. The distal edge is inserted into an opening accessing the disc and the first window is positioned to accommodate a laterally intruding portion of a first adjacent anatomical structure. The disc is access through an opening of the tube.

The method may also include selectively separating a second weakened portion from the remainder of the wall structure of the tube to form a second window. The second window extends from the distal edge of the wall portion. The second window is positioned to accommodate a laterally intruding portion of a second adjacent anatomical structure. The anatomical structures may be a spinous process and a facet.

The method may further include selectively separating a third weakened portion from the remainder of the wall structure of the tube to form a third window extending from a proximal edge of the wall portion.

Accessing the disc may also include angling an instrument extending through the opening at 30 degrees with respect to an axis of the opening. Also, the method may include accessing a contralateral portion of the disc.

These and other features and advantages of the implementations of the present disclosure will become more readily apparent to those skilled in the art upon consideration of the following detailed description and accompanying drawings, which describe both the preferred and alternative implementations of the present disclosure.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

Figure 1A:
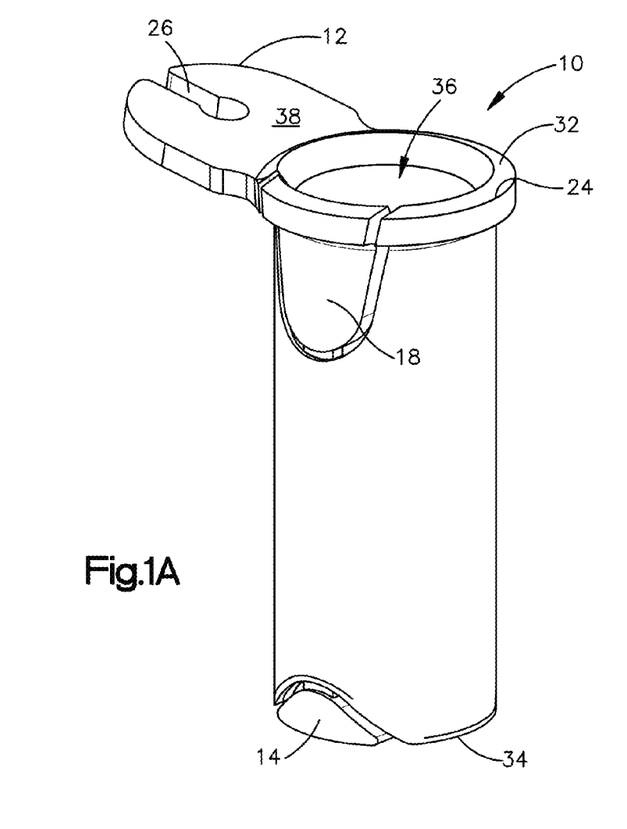
FIGS. 1A and 1B are perspective view of a surgical access tube.
Figure 1B:
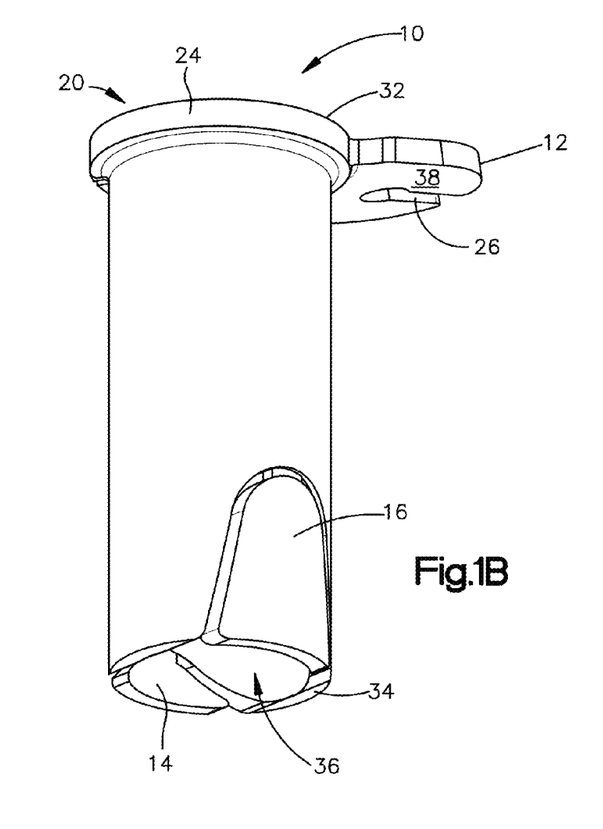
Figure 2:
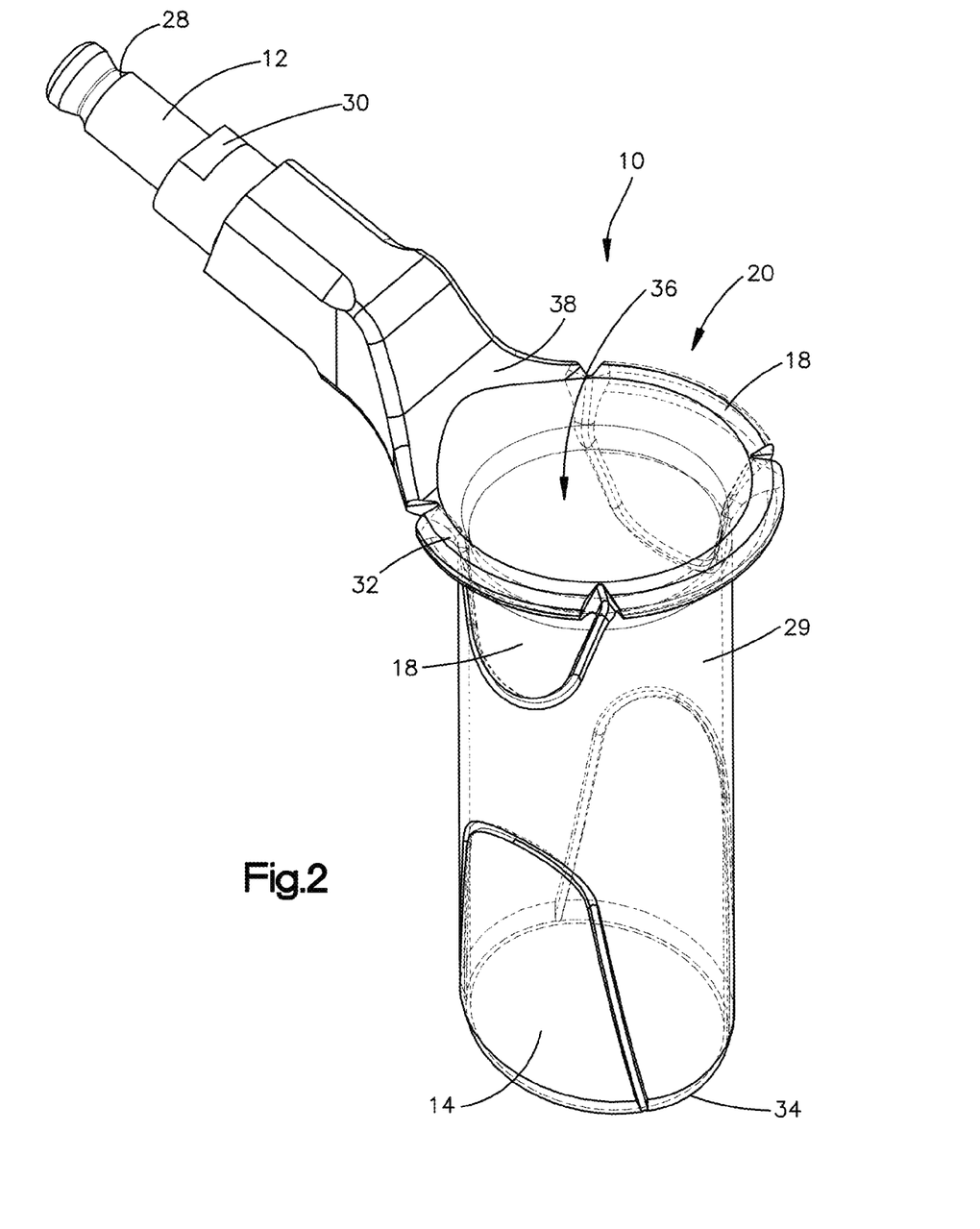
FIG. 2 is a perspective view of another surgical access tube with symmetrical windows.

An access tube 10, for example as shown in FIGS. 1A, 1B and 2, includes a wall structure and an optional handle 12 extending from the wall structure. Selectively weakened areas facilitate selective resection of the wall structure to reveal windows that accommodate lateral intrusions by surrounding anatomical structures and/or provide increased access to an intervertebral disc. For example, in FIG. 2, a first distal weakened portion 14 is configured to form a first window to afford lateral intrusion of a spinous process. A second distal weakened portion 16 is configured to form a second window to afford lateral intrusion of facet. A proximal weakened portion 18 is configured to afford additional angular access on a proximal end 20 of the tube.

Although discectomy is the surgical procedure illustrated herein using the access tube 10, other procedures may also benefit from having a modifiable access tube 10 with selective areas of weakness to allow onsite customization. For instance, the access tube 10 may be employed in port-access surgery through the ribs of a patient to obtain access to the heart for bypass procedures.

Referring again to FIGS. 1A and 1B, the access tube 10 includes the handle 12 and a wall structure 24. The handle 12 extends from a proximal end of the wall structure 24 and has the shape of a tab or flange with one or more openings or surfaces configured for engagement by instrumentation. In FIG. 1, the handle 12 defines a slot 26 with a circular opening at one end through which a pin of an extended instrument handle can be engaged. The pin, for example, may be attached to a rotating head that clamps down on the tab of the handle 12.

In another example, as shown in FIG. 2, the handle 12 may be a shaft with a plurality of engagement surfaces, such as an annular indentation 28 and anti-rotation flats 30 for gripping by a chuck mechanism of an extended instrument handle. The shaft may extend at an oblique angle from the proximal end of the wall structure 24 to afford gripping clearance between the extended instrumentation handle and the patient. At the same time, the obliquity of the angle facilitates use of the access tube 10 by elongate instrumentation in minimally-invasive surgical procedures such as intervertebral disc repair or dissection. At its distal end, the handle 12 of FIG. 2 flares outward to merge with the proximal end of the wall structure 24. This shape helps to reduce stress at the interface between the handle and walls structure.

Although two examples of the handle 12 are shown herein, it should be noted that the size and configuration of the handle can vary depending upon the type of surgery and preferences of the surgeon. Optionally, the access tube 10 may not include a handle at all and instead be gripped at some point(s) on its wall structure 24 by a fingers or a generally available surgical clamp or other instrumentation.

Figure 3:
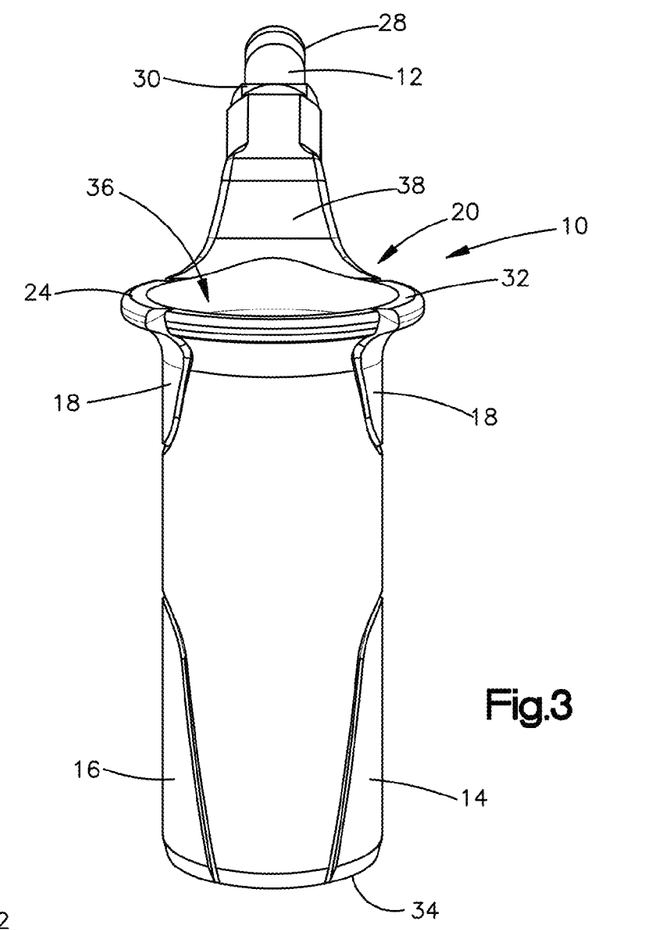
FIG. 3 is a perspective view of the surgical access tube of FIG. 2.
Figure 4:
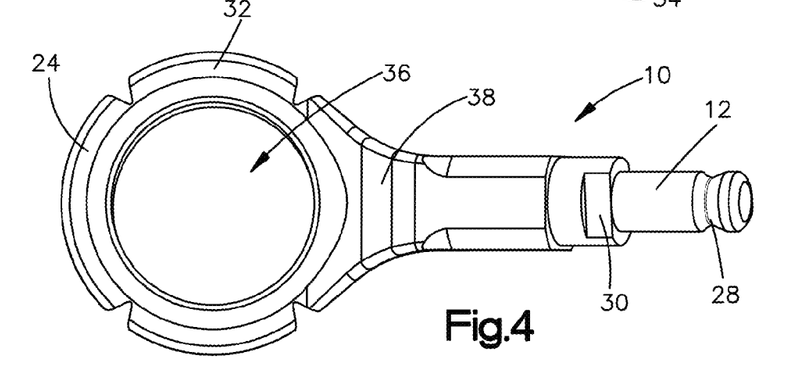
FIG. 4 is a top plan view of the surgical access tube of FIG. 2.

As shown in FIGS. 3 and 4, the wall structure includes a proximal edge 32, a distal edge 34 and a length extending therebetween. The wall structure is generally a right-angle cylinder and defines a cylindrical opening 36 extending therethrough. The opening 36 is sized to receive and facilitate access for various long-handled minimally invasive surgical instrumentation used for discectomies and other procedures. A cylindrical opening allows angle changes and different approaches with the surgical instrumentation.

An axis of the cylindrical opening may be generally oriented in the direction of the desired surgical site, such as the disc between two vertebra, for improved visibility and access. As will be described below, an advantage of the selective modifiability of the access tube 10, the axis of the opening 36 can be more directly oriented toward the desired surgical site. Thus, the surgeon can work in the center of the opening and not toward one side as in conventional tubes which risks damaging the tube or the instrument or limiting movement.

Although a cylindrical wall structure is illustrated herein, other wall structure 24 shapes could be used to define variations geometry of the opening 36. For example, the wall structure could be elliptical to afford better lateral access along the disc line or square or non-right angle cylindrical shapes depending upon the particular demands of the surgical procedure and instruments.

Referring again to FIG. 3 and to FIG. 4, the wall structure at the proximal edge 32 includes a flange 38 that merges into the handle 22. The flange extends outwards from the cylindrical shape and affords additional purchase for gripping by instrumentation and/or a guard against the access tube 10 slipping too deep within the surgical opening of the patient. At the distal edge 34, the wall structure 24 terminates as a slight taper and at a slight angle so as to be non-parallel with the proximal edge 32. The taper may help facilitate insertion through the tissues of the patient on the way to the surgical site.

The wall structure is constructed of a material with some stiffness to facilitate insertion into surgical openings and to hold back surrounding soft tissue structures to provide a path through the opening 36 to the surgical site. Such stiffness, for example, could come from metal or higher grade plastics. The material need not be entirely rigid, however, and could have some elasticity or flexibility as long as it facilitates passage through the opening 36. In addition, although the wall structure is shown with a solid, relatively impermeable surface, the materials or structure may have some permeability through the use of holes or permeable materials such as stiff films. For example, a porous plastic or metal screen material may be employed.

Manufacturing for a plastic part could include injection molding to form the walls structure and the die configured to form boundaries or structure of the weakened areas.

Positioned selectively on the walls structure are "weakened areas" which are areas of the tube that have been prepared to facilitate later selection and optional removal to form windows in the wall structure 24. Thus, the weakened areas may be areas of structural and/or chemical adaptation with thinner material, perforations or incised channels or lines, or that uses material that is brittle and more amenable to cracking or tearing either due to processing or composition. Also, the weakened areas may be more amenable to use of common surgical tools for removal and/or for hand removal.

Incised channels or lines, or perforations have the advantage of defining a fairly crisp or clean boundary. However, the weakened areas also need not have a well-defined boundary. The weakened areas could have properties that transition from one stiffness to another stiffness over a gradient wherein additional force is needed to tear or remove the weakened area further out from a centroid of the weakened area. Also, the weakened areas can overlap and need not be particularly discrete and/or have a specific, defined location other than that needed to facilitate access to the surgical site by the access tube 10 or the instruments passed therethrough.

The weakened areas may also have a plurality of incised lines that form a grid or set of discrete structures that could be snapped or broken off to achieve a customized window shape or size.

Referring to FIG. 1A and 1B again, the weakened areas include the proximal weakened portion 18, the first distal weakened portion 14 and the second distal weakened portion 16. The proximal weakened portion 18 is defined by a channel or line of materials removed or reduced in thickness to define a boundary. The proximal weakened portion extends from the proximal edge 32 at two points to define a saddle-shape with a rounded distal bottom arc on one lateral side of the wall structure 24 adjacent the handle 12.

First distal weakened portion 14 is positioned at the same circumferential location as the proximal weakened portion 18, as shown in FIG. 1A. The first distal weakened portion 14 has a shallow arc shape with a weakened line that extends up obliquely from the distal edge 34 to form a proximal arc 39 and then returns to the distal edge.

A saddle or rounded-V shape is formed by the weakened line at the second distal weakened portion 16. In particular, on the opposite circumferential location, a weakened line extends up from the distal edge 34 at a steep angle to form a proximal arc 39 and then returns at the same angle to the distal edge so as to define the second distal weakened portion 16.

The proximal arc 39 of the weakened portions 14, 16 may have a radius of up to 5 mm, or even 10 mm. For example, the proximal arc may have a 6 mm radius.

Figure 10:
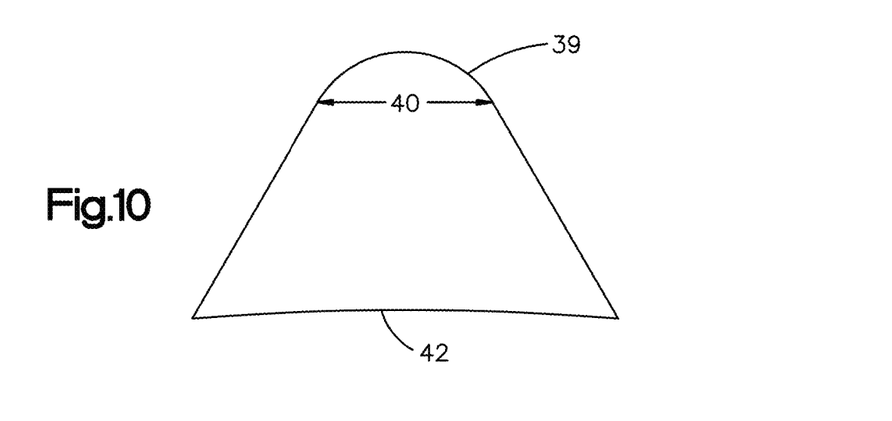
FIG. 10 is a schematic of geometry of a weakened portion.

As shown in FIG. 10, an exemplary weakened portion geometry has an arc base 40 defining where the arc 38 transitions to straight sides. For the first weakened portion 14, the arc base 40 may be 5 mm to 10 mm. For the second weakened portion 16, the arc base 40 may be 10 mm to 20 mm. For example, the arc base 40 may be 12 mm. (Note all such distances are defined herein as covering the straight chord length or along the curve.)

The exemplary weakened portion geometry also defines a distal base 42. For the first weakened portion 14, the distal base 42 is 10 mm to 20 mm. For the second weakened portion 16, the distal base 42 is 15 mm to 30 mm. For example, the distal base 42 may be 22 mm.

The exemplary weakened portion geometry 100 also has a sweep angle defined by the two side edges of the weakened portion extending from the arc base 40. For the first weakened portion 14, the sweep angle may be 90 degrees to 120 degrees. For the second weakened portion 16, the sweep angle may be 15 degrees to 30 degrees. These measurements could also be used for the proximal weakened portion 18.

FIGS. 3 and 4 show an implementation wherein the wall structure 24 has a symmetrical allocation of proximal and distal weakened portions. The proximal weakened portion 18 is duplicated on the opposite lateral side of the axis of the opening 36 and has the saddle-shape defined by weakened lines. At the distal end, the first and second distal weakened portions 14, 16 have the same saddle size and shape on opposite sides of the axis. In this manner, the same access tube 10 may be employed on either lateral side of a spinous process for a discectomy.

FIG. 4 shows a view of a V-shaped divot or channel that defines the proximal weakened portion 18 to facilitate separation from the rest of the wall structure 24.

Figure 5:
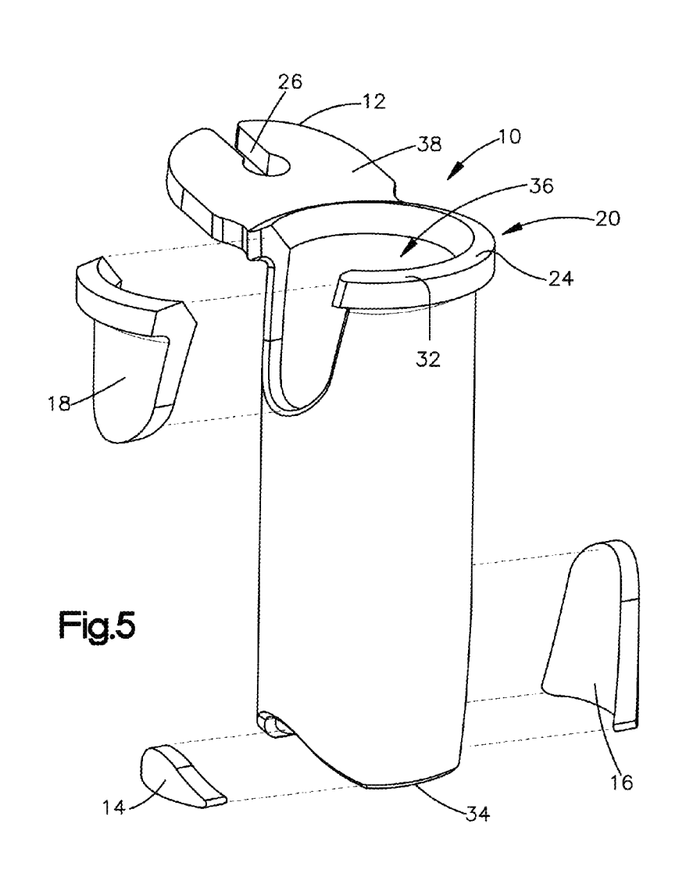
FIG. 5 is an exploded view of the surgical access tube of FIGS. 1A and 1B.
Figure 6:
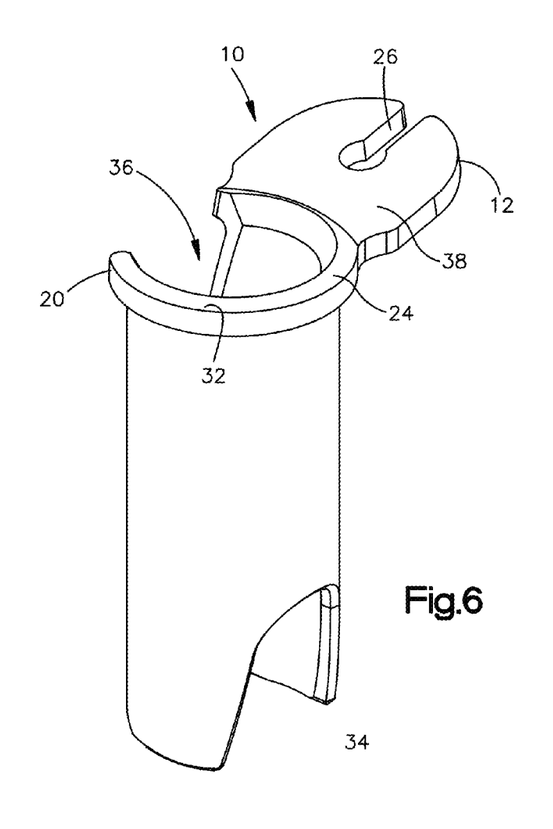
FIG. 6 is a perspective view of the surgical access tube of FIGS. 1A and 1B with weakened areas or portions removed to form windows.
Figure 7:
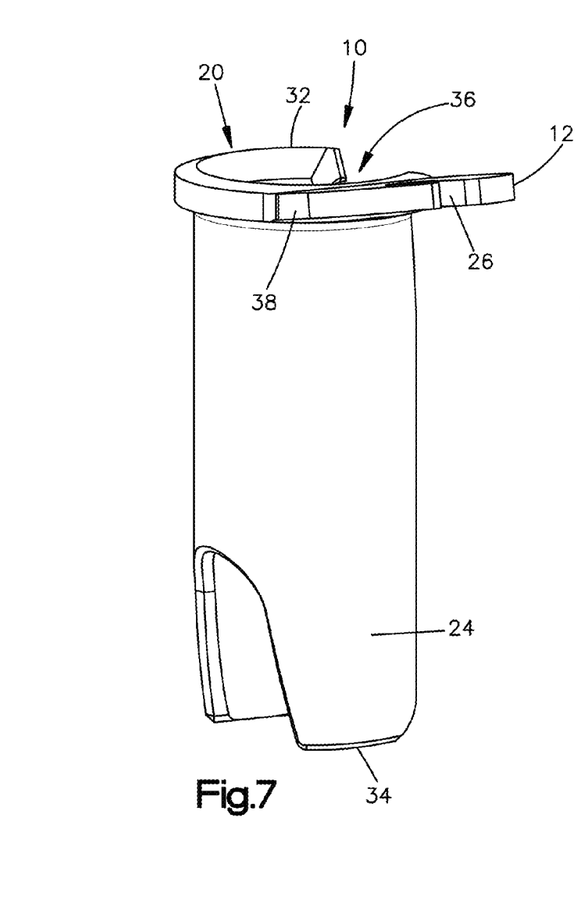
FIG. 7 is a perspective view of the surgical access tube of FIG. 2 with windows revealed.

Removal of the selectively weakened portions forms windows in the wall structure 24, as shown in FIGS. 5-7. Generally, the location of these windows improves the angle of insertion of the access tube 10 through the surgical opening to the surgical site. Or, they can improve the view of the surgical site and the range of angles for the surgical instruments working through the access tube 10.

For example, the access tube 10 without removal of the weakened portions allows for about 10 degrees of instrument angulation from the axis of the opening 36. Removal of the proximal weakened portion 18 to form a proximal window with a height of up to about 15 mm, or even up to 20 mm, opens the instrument angulation up to about 30 degrees on the same side as the weakened portion.

Figure 9:
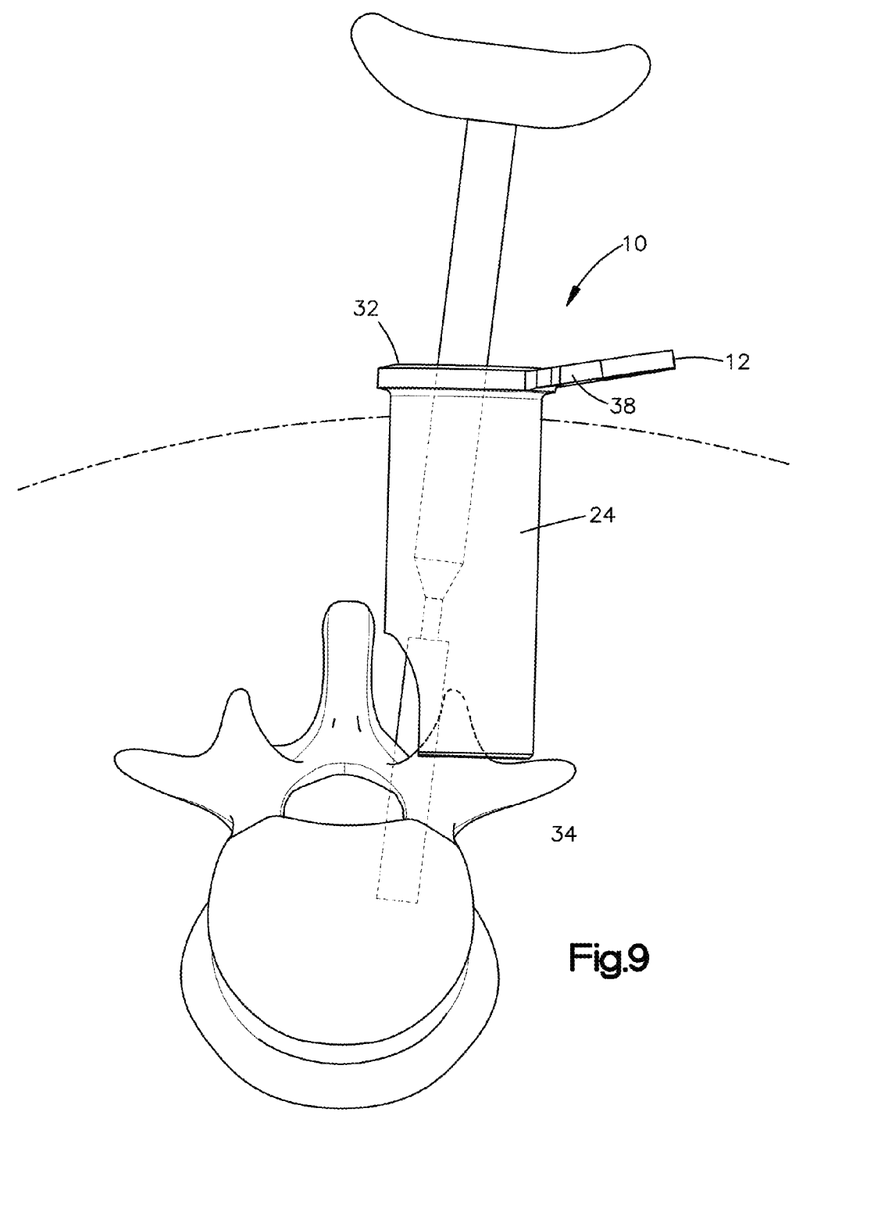
FIG. 9 is a schematic of a surgical discectomy procedure using a surgical access tube.

For example, for a 4 mm surgical instrument and a 60-70 mm tube height, the fully enclosed tube will provide about 12 degrees in instrument angulation. Use of the proximal and distal weakened areas together to create windows would allow 25 degrees of angulation. Angulation is also facilitated by stretching of the tissue at the proximal end of the tube for an additional 20 to 30 mm. Such improved angulation allows for contralateral access to the disc on the opposite side of the spinous process, as shown in FIG. 9.

Notably, not all of the weakened portions needs to be removed by a surgeon and instead could be selectively removed depending upon the particular anatomy or demands of the surgical process.

The larger weakened portion, such as the second distal weakened portion 16 in FIG. 1B or either distal weakened portion in FIG. 3, provides a window, when snapped off, that is relatively large to accommodate a spinous process and the associated lamina of the spine. The smaller window formed by first distal weakened portion 14 is relatively smaller and sized to accommodate the facet which is laterally positioned away from the spinous process.

The average height of a spinous process (and/or lamina) is about 32 mm and interference with a windowless access tube begins about halfway up the spinous process which includes a tapered lamina region that extends about 10 mm from the vertical portion of the spinous process. Therefore, an 18-20 mm (or even up to 30 mm) window height along the axis of the walls structure 24 provides clearance for the spinous process. The arc-length of the cutout is about 10 mm, or 110 degrees, of the distal edge 34.

The distance from the spinous process to the facet is about 10 mm, from a lateral view the facet has a radius of about 10 mm. The height of the facet window can range from 5 mm to 15 mm. For example, the height of the first weakened portion 14 (and corresponding facet window) is about 10 mm for a 22 mm diameter access tube 10. For smaller access tubes, about 19 mm in diameter, the facet window is about 8 mm in height.

The access tube could be even smaller, such as 16 mm in diameter, or other varied dimensions depending upon the different surgical applications. For example, the wall structure may be 28 mm, 22 mm, 19 mm or 16 mm or less in diameter. The height of the wall structure 24, i.e., the length, of the access tube may be about 60 mm to 70 mm, or even up to 90 mm, for the discectomy application. Notably, the height of the distal cutouts does not necessarily vary with the length of the tube as the anatomical features are not likely to change, only the skin depth.

The distal windows formed by removal of distal weakened portions 14, 16 are preferably oversized as an oversized cutout will still mate with the anatomical features while an undersized cutout might not work at all.

A height ratio of the larger window formed by removal of the second distal weakened portion 16 is about 1.8 to 3.75 times the height of the smaller window formed by the first distal weakened portion 14. This ratio is advantageous because of the relatively larger spinous process/lamina height versus the facet height. The ratio facilitates placement and centering for disc access.

Another advantageous ratio is a window height to access tube diameter. For example, the second distal weakened portion 16 height to access tube diameter may range from 1.875 for the taller window and smaller diameter tube to 0.71 for the shorter window and larger diameter tube. For example, the ratio may be 1.0 plus or minus 10% (i.e., 0.9 to 1.1). The first distal weakened portion 14 height to access tube diameter may range from 0.9375 to 0.18. For example, the ratio may be 0.42 to 0.45.

Figure 11A:
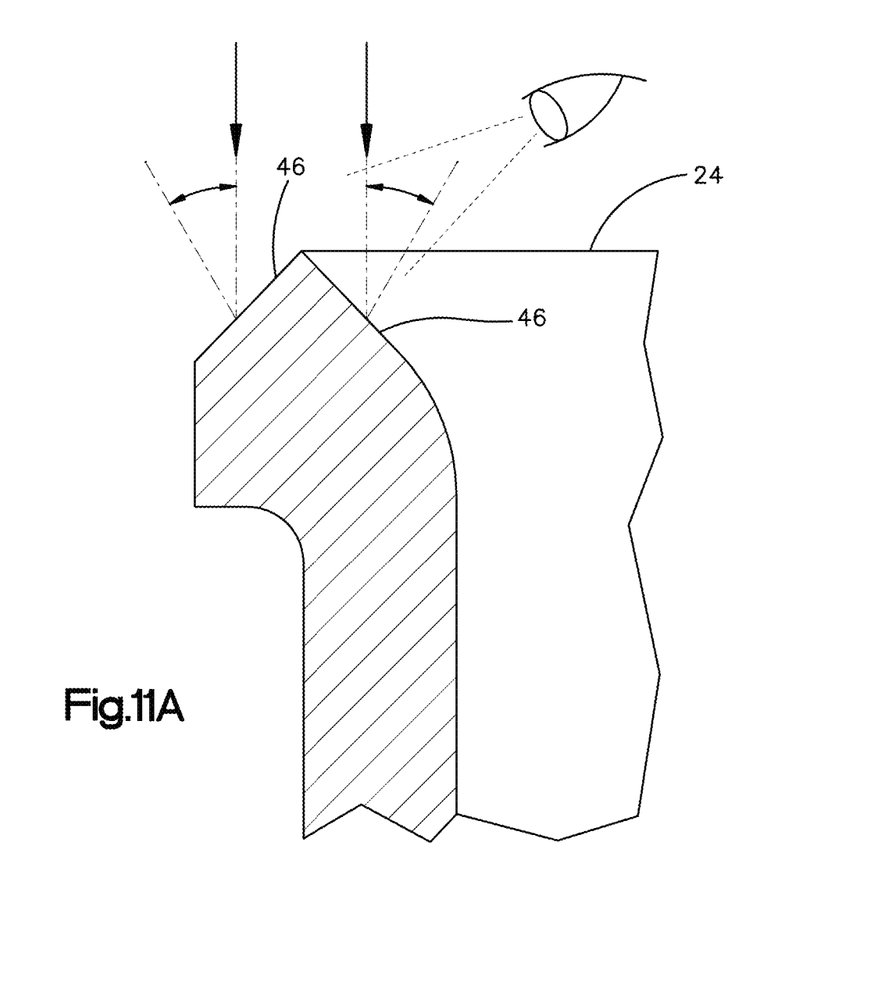
FIG. 11A is an enlarged sectional view of a proximal end of a microdiscectomy tube having anti-reflection surfaces.
Figure 11B:
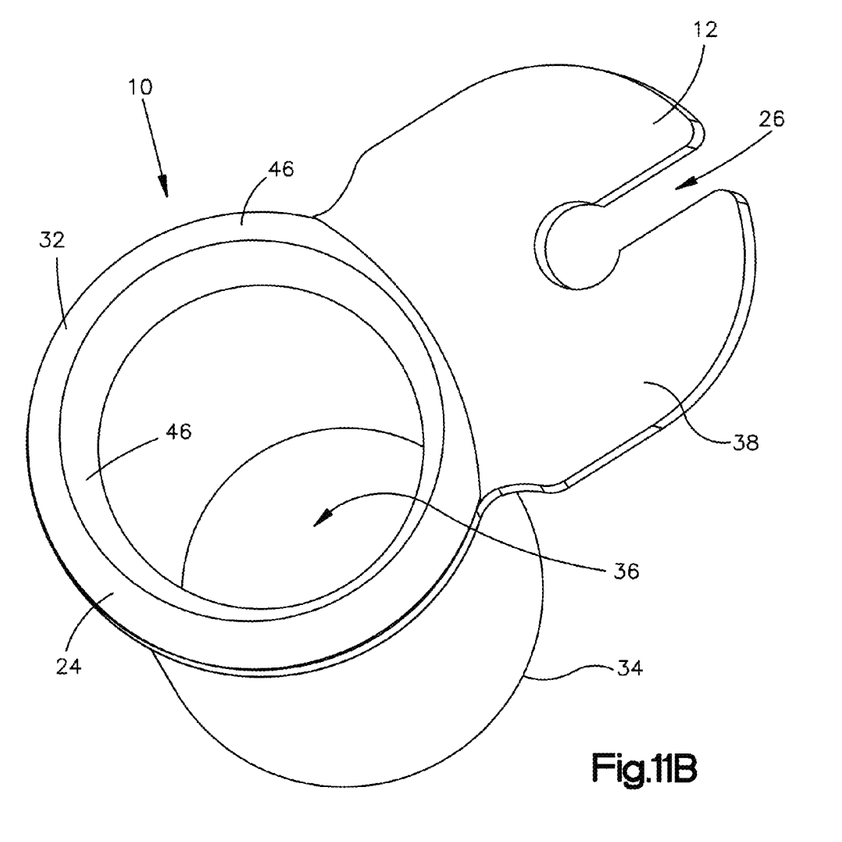
FIG. 11B is a perspective view of a proximal end of a microdiscectomy tube having anti-reflection surfaces.

Other adaptations include orienting proximal surfaces to reflect light away from the viewing angle, such as 30 degrees away from the viewing axis. FIGS. 11A and 11B, for example, show a sectional view and perspective view of a proximal end 20 of the access tube 10 having angled proximal surfaces 46 to deflect light away from sight lines. The proximal surfaces may be angled in a range of 30 degrees to 60 degrees, for example, from axially directed sign lines. The access tube 10 might also have a dark color and matte finish to further deflect light. The access tube 10 may also be an access tube that has no weakened areas or is otherwise a conventional access tube.

Figure 8:
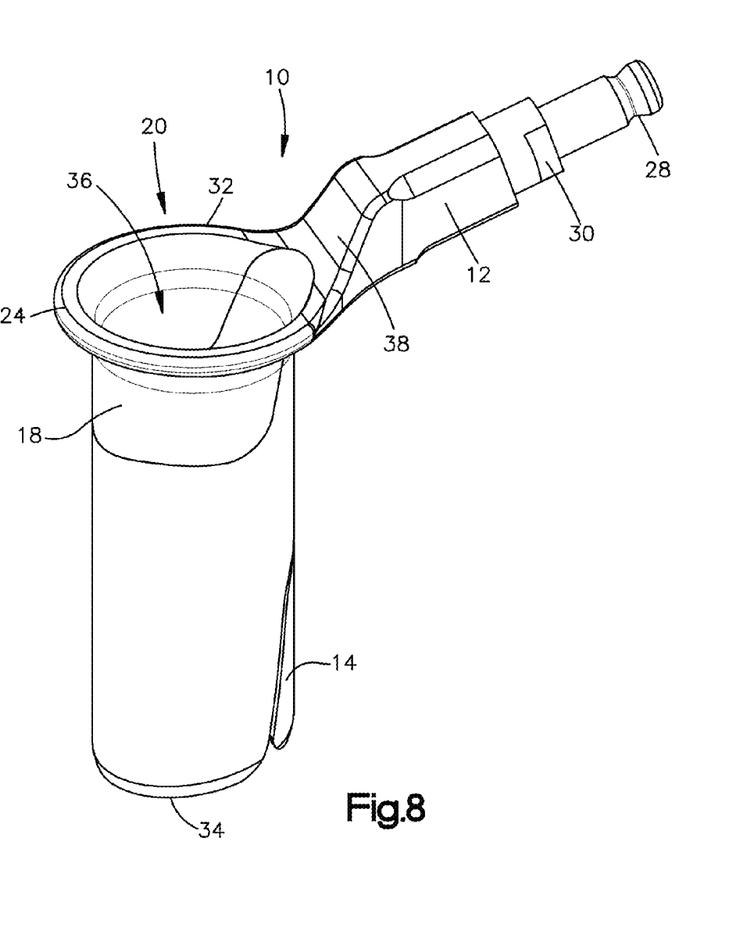
FIG. 8 is another surgical access tube with an elastic top wall portion.

FIG. 8 shows an access tube 10 that uses perforated weakened portions 14, 16 in hard plastic as described above but includes a flexible or resilient material for the proximal end of the walls structure 24. The elasticity of the proximal end would allow additional instrumentation angulation without having to form a window. The entire tube could also be manufactured of this elastic material for better angulation.

Figure 12A:
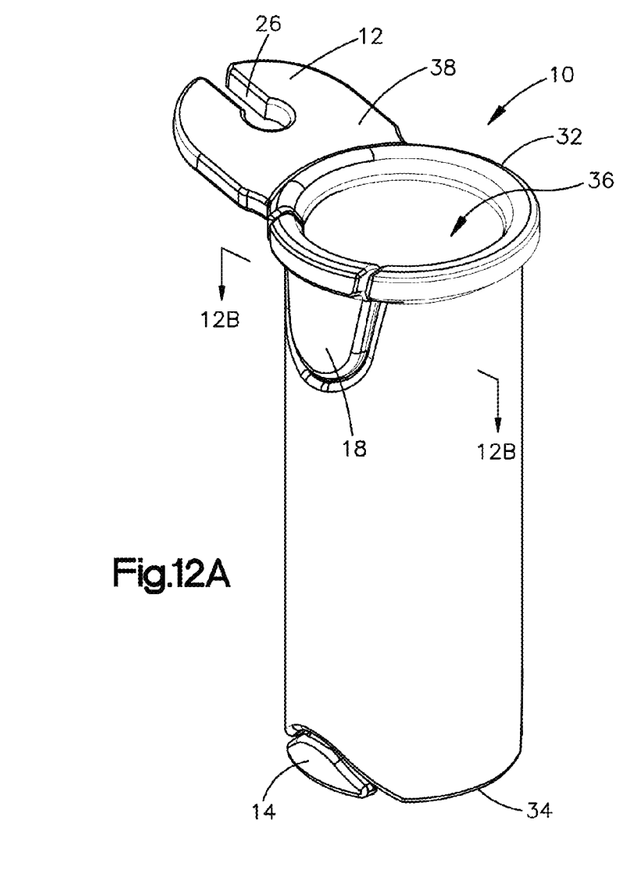
FIG. 12A is a perspective view of a surgical access tube.
Figure 12B:
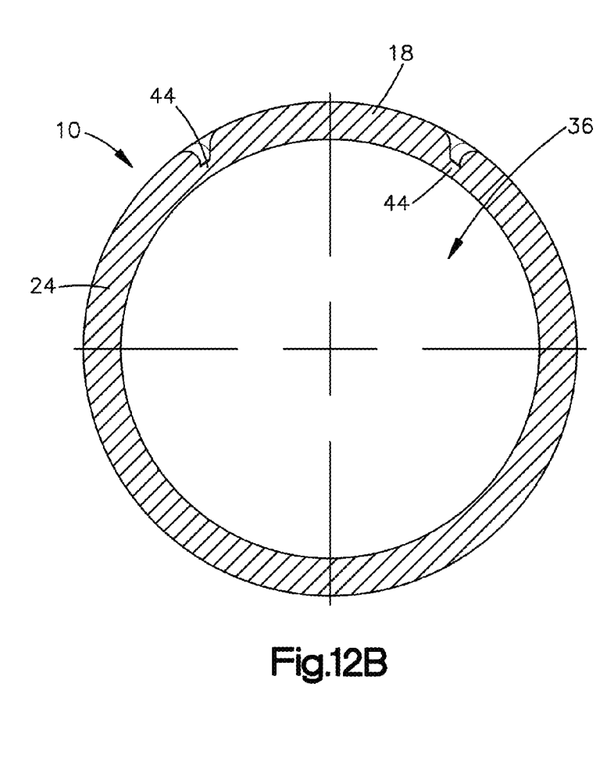
FIG. 12B is a cross-sectional view of the surgical access tube of FIG. 12A.

FIGS. 12A and 12B show an access tube with a web structure 44 extending between the weakened portion 18 (e.g., a tab) and the remaining wall structure 24. The web structure 44 is thin and connects the tabs to the tube wall structure 24. At the center of the tab 18 is a thicker flow runner to allow the plastic to flow into the tab area. During molding, the flow fronts from the tube and tab can meet at the thin web structure 44 and create knit lines in the area of the thin web. Web thickness could be structured as needed by application.

A discectomy procedure uses microsurgical instruments guided by fluoroscopy or other surgical imaging tools. A one to two cm longitudinal incision is made in the midline of the lower back, directly over the area of the herniated disc. Sequential dilation of the incision is performed with special tubes until the spine can be directly visualized using an operative microscope through a narrow tube.

A few millimeters of bone of the superior lamina may be removed to fully visualize the disc herniation. This also allows access to pinched nerves that are located within the spinal canal.

The access tube 10 may be employed when additional visualization and/or improved alignment is desired. Snapping off or removing the weakened portions 14, 16 provide windows for the spinous process, lamina and facet structures. In addition, the tube 10 prevents tissue creep under its distal edge 34 due to the tighter, more conforming placement.

Subsequently, the nerves are moved to the side and protected using specialized microsurgical instruments extended down the opening 36. The disc fragment or herniated disc portion is removed. The nerves may be examined and probed to ensure they are free of any further compression or other problems. The wound is washed out with antibiotics and the access tube 10 withdrawn.

A number of aspects of the systems, devices and methods have been described. Nevertheless, it will be understood that various modifications may be made without departing from the spirit and scope of the disclosure. Accordingly, other aspects are within the scope of the following claims.

That which is claimed:

1. A tube for facilitating access to an anatomical structure through intervening and adjacent anatomical structures, the tube comprising:
   a wall structure of material sufficiently stiff to define an hold open a tube opening to the anatomical structure through intervening anatomical structure; the wall structure including a proximal edge and a distal edge and a length extending therebetween;
   the wall structure including a plurality of window portions removably formed with the wall structure configured for separation from a remainder of the wall structure to form a window-shaped opening to accommodate medial or lateral intrusion into the tube opening of at least one of the anatomical structures, the plurality of window portions including:
   a first window portion located at the proximal edge of the wall structure configured to increase a viewing angle through the tube, the first window portion removably formed from the wall structure adjacent to a first weakened portion extending from the proximal edge and around the perimeter of the first window portion, and
   a second window portion located at the distal edge of the wall structure configured to increase a viewing angle through the tube, the second window portion removably formed with the wall structure adjacent to a distal weakened portion extending from the distal edge and around a perimeter of the second window portion.
   the first weakened portion is positioned at the same circumferential location as the distal weakened portion, and a second distal weakened portion positioned at an opposite circumferential location from the first weakened portion, each distal weakened portion forms a proximal arc which transitions to straight sides to intersect the distal edge of the tube, the first distal weakened portion having an arc base 5mm to 10mm long, the second distal weakened portion having an arc base 10mm to 20mm long, the second distal weakened portion having a height 1.8 to 3.75 times the height of the first distal weakened portion.

2. A tube of claim 1, further comprising a third window portion located proximate the distal edge of the wall structure configured to increase a viewing angle through the tube, the third window portion removably formed with the wall structure adjacent to the second distal weakened portion.

3. A tube of claim 2, wherein the third window portion has a maximum height of 30 mm.

4. A tube of claim 2, wherein the second window portion is positioned to create a facet window and the third window portion located proximate the distal edge is positioned to create a spinous process window.

5. A tube of claim 4, wherein the spinous process window and facet window are positioned on opposite sides of the wall structure.

6. A tube of claim 5, wherein the facet window has a proximal arc shape.

7. A tube of claim 6, wherein the proximal arc shape has a radius of up to 10 mm.

8. A tube of claim 5, wherein the second and third windows are asymmetrical.

9. A tube of claim 8, wherein the spinous process window has a height of 50% or less a height of a spinous process.

10. A tube of claim 9, wherein the height of the spinous process window is 30 mm or less.

11. A tube of claim 10, wherein the facet window has a height of 15 mm or less.

12. A tube of claim 10, wherein the spinous process window is configured to accommodate a spinous process/lamina tapered region.

13. A tube of claim 10, wherein the spinous process window has a proximal arc shape.

14. A tube of claim 13, wherein the proximal arc shape has a radius of up to 10 mm.

15. A tube of claim 4, wherein the spinous process window has a height 1.8 to 3.75 times a height of the facet window.

16. A tube of claim 2, wherein the wall structure has a diameter and the third window portion has an axial height and a first ratio of the axial height to diameter is from 0.18 to 1.875.

17. A tube of claim 16, wherein the second window portion is positioned to create a facet window and a second ratio is 0.18 to 0.9375.

18. A tube of claim 17, wherein the second ratio is 0.42 to 0.45.

19. A tube of claim 16, wherein the first ratio is 0.71 to 1.875.

20. A tube of claim 19, wherein the first ratio is 0.9 to 1.1.

21. A tube of claim 2, wherein a third window portion is located proximate the distal edge has a sweep angle of 15 degrees to 30 degrees.

22. A tube of claim 2, wherein the first and third window portions are asymmetrical.

23. A tube of claim 1, wherein the first window portion allows 30 degrees of viewing angle from the proximal edge.

24. A tube of claim 1, wherein the selectively weakened portion encompasses a total of at least 110 degrees of the distal edge.

25. A tube of claim 1, wherein the selectively weakened portion extends through a full thickness of the wall structure.

26. A tube of claim 1, wherein the length is 90 mm or less.

27. A tube of claim 26, wherein the wall structure is cylindrical and has a diameter of 19 mm or less.

28. A tube of claim 1, wherein a side of the second window portion defines a sweep angle of between 15 degrees and 120 degrees.

29. A tube of claim 28, wherein the window portion has a sweep angle of 90 degrees to 120 degrees.

30. A tube of claim 1, wherein the proximal edge of the wall structure includes light deflecting surfaces that are configured to deflect light at least 30 degrees away from an axis of the wall structure.

31. A tube of claim 30, wherein all surfaces of the proximal edges are light deflecting surfaces.

32. A tube of claim 31, wherein the wall structure has a reflection reducing finish.

33. A tube of claim 30, wherein the wall structure includes a color darker than white.

34. A tube of claim 1, wherein the proximal edge of the wall structure includes antireflective surfaces.

35. A tube of claim 34, wherein the antireflective surfaces are at least angled 30 degrees away from a sight line.

36. A tube of claim 1, wherein the wall structure defines an annular structure having a substantially constant cross-section along the length of the wall structure.

37. A tube of claim 1, wherein the wall structure is cylindrical and defines a substantially constant diameter along the length.

38. A tube of claim 1, wherein the wall structure defines a curvilinear shape in cross-section having a substantially constant cross-section along the length of the wall structure.

39. A tube for facilitating access to an anatomical structure through intervening and adjacent anatomical structures, the tube comprising:
  a wall structure of material sufficiently stiff to define and hold open a tube opening to the anatomical structure through intervening anatomical structure;
  the wall structure including a proximal edge and a distal edge and a length extending therebetween, the wall structure defining an annular structure having a substantially constant cross-section along the length,
  the proximal edge including light deflecting surfaces configured to deflect light at least 30 degrees away from an axis of the wall structure, the light deflecting surfaces including:
    a first light deflecting surface extending from the proximal edge to an inner surface of the tube opening at an angle between 30 and 60 degrees with respect to a longitudinal axis of the tube, and
    a second light deflecting surface adjacent to the first light deflecting surface, the second light deflecting surface extending from the proximal edge towards an outer surface of the tube at an angle between 30 and 60 degrees with respect to the longitudinal axis of the tube, the wall structure including a plurality of window portions removably formed with the wall structure configured for separation from a remainder of the wall structure to form a window-shaped opening to accommodate medial or lateral intrusion into the tube opening of at least one of the anatomical structures, the plurality of window portions including:
  a first window portion located at the proximal edge of the wall structure configured to increase a viewing angle through the tube, the first window portion removably formed from the wall structure adjacent to a first weakened portion extending from the proximal edge and around a perimeter of the first window portion, and
  a second window portion located at the distal edge of the wall structure configured to increase a viewing angle through the tube, the second window portion removably formed with the wall structure adjacent to a distal weakened portion extending from the distal edge and around a perimeter of the second window portion.

the first weakened portion is positioned at the same circumferential location as the distal weakened portion, and a second distal weakened portion positioned at an opposite circumferential location from the first weakened portion, each distal weakened portion forms a proximal arc which transitions to straight sides to intersect the distal edge of the tube, the first distal weakened portion having an arc base 5mm to 10mm long, the second distal weakened portion having an arc base 10mm to 20mm long, the second distal weakened portion having a height 1.8 to 3.75 times the height of the first distal weakened portion.

40. A tube of claim 39, wherein all surfaces of the proximal edge are light deflecting surfaces.

41. A tube of claim 39, wherein the wall structure includes a color darker than white.

42. A tube of claim 39, wherein the wall structure has a reflection reducing finish.

\* \* \* \* \*

UNITED STATES PATENT AND TRADEMARK OFFICE
CERTIFICATE OF CORRECTION

PATENT NO.       : 9,968,348 B2
APPLICATION NO.  : 13/775571
DATED            : May 15, 2018
INVENTOR(S)      : Daniel Vennard et al.

Page 1 of 1

It is certified that error appears in the above-identified patent and that said Letters Patent is hereby corrected as shown below:

In the Claims

Claim 1 - Lines 4-5 "a wall structure of material sufficiently stiff to define an hold open" should be "a wall structure of material sufficiently stiff to define and hold open...";

Claim 1 - Line 21 "and around the perimeter of the first window portion" should be "and around a perimeter of the first window portion";

Claim 24 should read "A tube of claim 1, wherein the second distal weakened portion encompasses a total of at least 110 degrees of the distal edge.";

Claim 25 should read "A tube of claim 1, wherein all weakened portions extend through a full thickness of the wall structure";

Claim 29 should read "A tube of claim 28, wherein the second window portion has a sweep angle of 90 degrees to 120 degrees".

Signed and Sealed this
Ninth Day of April, 2019

Andrei Iancu
*Director of the United States Patent and Trademark Office*